(12) United States Patent
Vrettos et al.

(10) Patent No.: US 6,671,345 B2
(45) Date of Patent: Dec. 30, 2003

(54) DATA ACQUISITION FOR COMPUTED TOMOGRAPHY

(75) Inventors: Chris J. Vrettos, Willoughby, OH (US); Marc A. Chappo, Elyria, OH (US); Anthony F. Krecic, Euclid, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/045,450

(22) Filed: Nov. 7, 2001

(65) Prior Publication Data

US 2002/0141530 A1 Oct. 3, 2002

Related U.S. Application Data

(60) Provisional application No. 60/248,457, filed on Nov. 14, 2000.

(51) Int. Cl.[7] ............................................... A61B 6/00
(52) U.S. Cl. ......................................... 378/19; 378/98.8
(58) Field of Search .................. 250/370.09, 370.08, 250/370.11; 341/155, 157, 172; 378/19, 98.8, 4

(56) References Cited

U.S. PATENT DOCUMENTS

| | | | | |
|---|---|---|---|---|
| 3,921,012 A | * | 11/1975 | Marshall, III | 327/101 |
| 5,045,685 A | * | 9/1991 | Wall | 250/208.1 |
| 5,084,639 A | | 1/1992 | Ribner | |
| 5,099,239 A | * | 3/1992 | Bruce et al. | 341/155 |
| 5,323,439 A | * | 6/1994 | Nobuta et al. | 378/19 |
| 5,592,523 A | * | 1/1997 | Tuy et al. | 378/19 |
| 5,602,468 A | | 2/1997 | Harrington | |
| 5,880,691 A | * | 3/1999 | Fossum et al. | 341/162 |
| 5,991,358 A | * | 11/1999 | Dolazza et al. | 378/19 |
| 6,115,448 A | * | 9/2000 | Hoffman | 378/19 |
| 6,335,958 B1 | * | 1/2002 | Munier et al. | 378/19 |
| 6,362,480 B1 | * | 3/2002 | Peter et al. | 250/366 |
| 6,389,097 B1 | * | 5/2002 | Bulkes et al. | 378/19 |
| 6,396,898 B1 | * | 5/2002 | Saito et al. | 378/19 |
| 6,426,991 B1 | * | 7/2002 | Mattson et al. | 378/19 |

FOREIGN PATENT DOCUMENTS

| | | |
|---|---|---|
| DE | 199 45 757 A1 | 9/1999 |
| EP | 0 715 830 A1 | 6/1996 |
| WO | WO 00/25149 | 5/2000 |

OTHER PUBLICATIONS

Analog–Digital Conversion Handbook, Third Ed. (MA: Prentice Hall, 1986), p. 32–35.*
PCT International Search Report for International application No. PCT/US 01/47097.

* cited by examiner

Primary Examiner—Drew A. Dunn
Assistant Examiner—Courtney Thomas
(74) Attorney, Agent, or Firm—Thomas M. Lundin, Esq.

(57) ABSTRACT

A computerized tomographic imaging system including a stationary gantry portion defining an examination region and a rotating gantry portion for rotation about the examination region. An x-ray source is disposed on the rotating gantry portion for projecting x-rays through the examination region. A plurality of modular radiation detector units are disposed across the examination region from the x-ray source. Each radiation detector unit includes an array of x-ray sensitive cells for receiving radiation from the x-ray source after it has passed through the examination region and for generating an analog signal indicative of the radiation received thereby. Each radiation detector unit also includes a plurality of integrated circuits connected to the x-ray sensitive cells with each integrated circuit including a plurality of channels. Each channel receives the analog signal from an x-ray sensitive cell and generates digital data indicative of the value of the analog signal.

74 Claims, 6 Drawing Sheets

DATA ACQUISITION FOR COMPUTED TOMOGRAPHY

This application claims the benefit of U.S. Provisional Application No. 60/248,457, filed Nov. 14, 2000.

BACKGROUND

The present invention relates to the field of medical imaging and has particular applicability to computed tomography (CT). The invention also finds application in the fields of x-ray detection and imaging, including industrial inspection systems, non-destructive testing, baggage inspection, and the like.

Early CT scanners had only a single pencil beam x-ray source for transmitting x-rays through an examination region and a single detector for receiving attenuated x-rays after they had passed through a patient in the examination region. The source and detector were repeatedly rotated and translated about the examination region to obtain an image of the patient. The process of obtaining images with these scanners was slow and resulted in low resolution images.

Subsequent developments in CT technology have been made to decrease scanning time, increase patient throughput, and increase spatial resolution of images. These goals have been accomplished by, among other things, increasing the size of the beam radiation generated by the x-ray source and by increasing the number of detectors in a scanner.

As with the early scanners, second generation scanners used a rotation-translation system, but improved on the data acquisition speed of the earlier scanners through the use of an array of detectors and a small fan-beam x-ray source.

Third generation CT scanners also used a fan-beam x-ray source and an array of detectors that rotated simultaneously about the subject. However, the fan-beam of the third generation scanner was wide enough to cover the cross-section of a region of interest of the patient. Therefore, there was no need to translate the source-detector assembly.

Like the third generation scanners, fourth generation CT scanners used a fan-beam x-ray source that rotated about the examination region. However, the detectors were distributed around the examination region and did not rotate with the x-ray source.

Regardless of the configuration, CT scanners included at least one discrete radiation detector which converted x-ray radiation which traversed the patient examination area into electronic signals. Each radiation detector included a x-ray sensitive face, such as a scintillation crystal, which converted the received radiation into a corresponding quantity of light. A solid state photodiode was provided to convert the light emitted by the scintillation crystal into analog electrical signals indicative of the intensity of the crystal emitted light, hence the intensity of the received radiation.

In the case of multi-slice imaging, a two-dimensional array of radiation detectors was used. The radiation detectors were separately arranged on a circuit board. Each circuit board supported an array of photodiodes and attached scintillation crystals. In addition, a preamplifier was operatively connected to the circuit board and connected to each photodiode output to convert the photodiode current to an appropriate voltage within the dynamic range of the analog-to-digital conversion system.

The analog signals from the circuit board were carried to a separate processing area where they were converted from their analog state into a corresponding digital signal. The processing area was typically located some distance from the detectors. The analog signals were carried to the processing area via a relatively long bus system which extended from the photodiode to the analog-to-digital converter.

One problem with such a system relates to degradation of the analog signals as they travel over the long bus system between the radiation detectors and the processing area.

CT scanners operate in an environment of extraneous radio frequency electromagnetic signals, the frequencies of which vary over a wide band. Sources of extraneous signals include nearby operating electrical components, equipment, signals from other detectors, and the like. The long bus systems include long lead wires which inadvertently act as antennas in picking up extraneous electromagnetic signals and converting them into analog signals. The extraneous analog signals are superimposed on and mix with the analog signals from the detectors. The superimposed extraneous signals appear as noise and fictitious data when reconstructed into images. The resulting images are degraded by noise, ghosting, and other artifacts.

Another problem relates to the complexity of the electronic circuitry associated with the detectors as the number of detectors increased.

Each detector normally required a separate channel with all of the front end electronics and hardware to support the detector. As the number of detectors increased, the circuitry and associated electrical connections required to process and transfer the signals generated by the detectors increased as well. Therefore, implementing a large numbers of detectors has been a difficult task.

SUMMARY

Those skilled in the art will, upon reading and understanding the appended description, appreciate that aspects of the present invention address the above and other matters.

In accordance with one aspect of the present invention, a computerized tomographic imaging system is provided. The system includes a stationary gantry portion defining an examination region and a rotating gantry portion for rotation about the examination region. An x-ray source is disposed on the rotating gantry portion for projecting x-rays through the examination region and a plurality of modular radiation detector units are disposed across the examination region from the x-ray source. Each radiation detector unit includes an array of x-ray sensitive cells for receiving radiation from the x-ray source after it has passed through the examination region and for generating an analog signal indicative of the radiation received thereby. Each radiation detector unit also includes a plurality of integrated circuits connected to the x-ray sensitive cells with each integrated circuit including a plurality of channels. Each channel receives the analog signal from an x-ray sensitive cell and generates digital data indicative of the value of the analog signal.

In accordance with a more limited aspect of the present invention, each modular radiation detector unit also includes a circuit board and the plurality of x-ray sensitive cells and plurality of integrated circuits are disposed on the circuit board.

In accordance with a more limited aspect of the present invention, the integrated circuits are disposed on the circuit board so that the variability of the distances from the x-ray sensitive cells to their respective integrated circuits is minimized.

In accordance with a more limited aspect of the present invention, each integrated circuit includes at least thirty-two channels.

In accordance with a more limited aspect of the present invention, each channel includes a ratiometric current to frequency converter which generates a number of electrical pulses during a time period, the number of pulses being proportional to the magnitude of the analog signal.

In accordance with a more limited aspect of the present invention, each channel also includes a frequency to digital converter which generates a first digital value indicative of the number of pulses generated during the time period and a second digital value indicative of a period of time between a first pulse and a last pulse of the time period.

In accordance with a more limited aspect of the present invention, each channel comprises a parallel to serial converter, the parallel to serial converter including means for interconnecting the channels so that the digital data from a plurality of the channels are combined to form a single output stream of digital data.

In accordance with a more limited aspect of the present invention, the array of x-ray sensitive cells is an array having M rows and N columns, M and N being integers greater than or equal to two.

In accordance with a more limited aspect of the present invention, each row of the array of x-ray sensitive cells corresponds to a single slice of image data.

In accordance with a more limited aspect of the present invention, at least one row of x-ray sensitive cells is connected to one of the integrated circuits.

In accordance with another aspect of the present invention, a CT imaging system is provided. The CT imaging system includes a gantry defining an examination region and an x-ray source for projecting x-rays through the examination region. The system also includes a plurality of x-ray sensitive cells for converting x-rays that pass through the examination region into a plurality of analog signals. A plurality of integrated circuits are in electrical connection with the x-ray sensitive cells and each integrated circuit receives the analog signals and generates digital data indicative of the values of the analog signals. The integrated circuits are disposed at the perimeter of the examination region and include means for interconnecting the integrated circuits so that the digital data from a plurality of the integrated circuits are combined to form a single output stream of digital data.

In accordance with a more limited aspect of the present invention, each integrated circuit also includes a plurality of channels with each channel having an analog to digital converter for converting the analog signal of a single x-ray sensitive cell to digital data.

In accordance with a more limited aspect of the present invention, each channel also includes a ratiometric current to frequency converter for generating a number of electrical pulses during a time period. The number of pulses are proportional to the magnitude of the analog signal.

In accordance with a more limited aspect of the present invention, each channel also includes a frequency to digital converter which generates a first digital value indicative of the number of pulses generated during the time period and a second digital value indicative of a period of time between a first pulse and a last pulse of the time period.

In accordance with a more limited aspect of the present invention, the CT imaging system also includes means to assure that the value of the first digital value is at least two.

In accordance with a more limited aspect of the present invention, each channel also includes a parallel to serial converter for outputting the digital data in a serial output stream.

In accordance with a more limited aspect of the present invention, the CT imaging system also includes a plurality of circuit boards disposed at the perimeter of the examination region and the x-ray sensitive cells and the integrated circuits are disposed on the circuit boards.

In accordance with another aspect of the present invention, a CT imaging system is provided which includes a stationary gantry portion, a rotating gantry portion for rotation about an examination region, an x-ray source disposed on the rotating gantry portion for projecting x-rays through the examination region, a plurality of x-ray sensitive cells disposed across the examination region from the x-ray source for receiving x-rays originating at the x-ray source and generating analog signals indicative of the x-rays received thereby, and at least one integrated circuit disposed in proximity to the x-ray detectors. The integrated circuit includes a plurality of channels with each channel coupled to a single x-ray sensitive cell for receiving the analog signal from the cell and for generating digital data indicative of the value of the analog signal.

In accordance with a more limited aspect of the present invention, the plurality of x-ray sensitive cells and the integrated circuit are disposed on a circuit board.

In accordance with a more limited aspect of the present invention, the plurality of x-ray sensitive cells are arranged in a two-dimensional array.

In accordance with a more limited aspect of the present invention, the two-dimensional array includes at least two rows and at least two columns of x-ray sensitive cells.

In accordance with a more limited aspect of the present invention, each channel includes a ratiometric current to frequency converter which generates a number of electrical pulses during a time period, the number of pulses is proportional to the magnitude of the analog signal received by the channel.

In accordance with a more limited aspect of the present invention, each channel also includes a frequency to digital converter which generates a first digital value indicative of the number of pulses generated during the time period and a second digital value indicative of a period of time between a first pulse and a last pulse of the time period.

In accordance with a more limited aspect of the present invention, each channel includes a parallel to serial converter for outputting the digital data of a plurality of x-ray sensitive cells in a serial output stream.

In accordance with a more limited aspect of the present invention, the integrated circuit also includes means for receiving digital data from a second integrated circuit. The received digital data is indicative of the values of the analog signals of the second integrated circuit. The integrated circuit also includes means for sending digital data to a third integrated circuit, the sent digital data being indicative of the values of the analog signals of the integrated circuit.

In accordance with another aspect of the present invention, a computerized tomographic imaging system is provided. The CT imaging system includes a stationary gantry portion having an examination region and a rotating gantry portion for rotation about the examination region. The system also includes an x-ray source mounted to the rotating gantry portion for projecting x-rays through the examination region and a plurality of radiation detector units disposed across the examination region from the x-ray source. Each radiation detector unit includes a circuit board and x-ray detector means for generating analog signals indicative of radiation that passes from the x-ray source to the radiation detector unit. The x-ray detector means includes a two dimensional array of x-ray sensitive cells and is disposed on the circuit board. Each radiation detector unit also includes multi-channel analog to digital conversion means for converting the analog signals to digital data. Each channel of the multi-channel analog to digital conversion means is connected to a single x-ray sensitive cell and the multi-channel analog to digital conversion means is disposed on the circuit board.

In accordance with a more limited aspect of the present invention, each channel includes a ratiometric current to frequency converter for generating a number of electrical pulses during a time period. The number of pulses is proportional to the magnitude of the analog signal.

In accordance with a more limited aspect of the present invention, each channel also includes a frequency to digital converter which generates a first digital value indicative of the number of pulses generated during the time period and a second digital value indicative of a period of time between a first pulse and a last pulse of the time period.

In accordance with a more limited aspect of the present invention, each channel includes a parallel to serial converter for outputting the digital data of the two-dimensional array of x-ray sensitive cells in a serial output stream.

In accordance with a more limited aspect of the present invention, each array of x-ray sensitive cells includes a number of rows and a number of columns and each row corresponds to a single slice of image data.

In accordance with a more limited aspect of the present invention, the multi-channel analog to digital conversion means includes at least one integrated circuit and the x-ray sensitive cells of one row of the array of x-ray sensitive cells are connected to the same integrated circuit.

In accordance with another aspect of the present invention, a method of computerized tomographic imaging is provided. The method includes projecting x-rays through an examination region using an x-ray source and detecting the projected x-rays after they have crossed the examination region using a plurality of x-ray sensitive cells disposed on a circuit board. The plurality of x-ray sensitive cells each generate a corresponding analog signal indicative of the x-rays detected thereby. The method also includes converting the analog signals to digital data using at least one integrated circuit. The integrated circuit includes multiple channels for analog to digital conversion of the analog signals and is disposed on the circuit board. Each channel converts the analog signal of a single x-ray sensitive cell.

In accordance with a more limited aspect of the present invention, the method of CT imaging also includes the step of generating a serial data stream including the digital data from a plurality of x-ray sensitive cells with the step of generating a serial data stream being performed using the integrated circuit.

In accordance with a more limited aspect of the present invention, the step of converting the analog signals to digital data includes, for each x-ray sensitive cell, storing a first value representing a number of pulses during a time period, the pulses occurring when the analog signal from each cell reaches a threshold value, and storing a second value indicative of the time between a first pulse and a last pulse that occur during the time period.

In accordance with a more limited aspect of the present invention, the method of CT imaging also includes the step of assuring that at least two pulses occur during the time period.

In accordance with another aspect of the present invention, a method of CT imaging is provided which includes rotating an x-ray source about an examination region, projecting x-rays through the examination region using the x-ray source, and detecting the projected x-rays using a plurality of two-dimensional arrays of x-ray sensitive cells. The arrays of x-ray sensitive cells is disposed on a plurality of circuit boards with each x-ray sensitive cell generating an analog signal indicative of the x-rays detected by the cell. The method also includes the step of generating digital signals indicative of the analog signals using a plurality of integrated circuits. The integrated circuits are disposed on the circuit boards and each integrated circuit includes a plurality of channels with each channel converting to digital the analog signal from not more than one x-ray sensitive cell.

In accordance with a more limited aspect of the present invention, the method of CT imaging also includes the step of generating a single output stream of the digital data by interconnecting the channels of the integrated circuits.

In accordance with a more limited aspect of the present invention, each channel of the integrated circuits includes a ratiometric current to frequency converter.

In accordance with a more limited aspect of the present invention, each channel also includes a frequency to digital converter for generating a number of electrical pulses during a time period. The number of pulses is proportional to the magnitude of the analog signal.

In accordance with a more limited aspect of the present invention, the method of CT imaging also includes the step of generating a first digital value indicative of a number of electrical pulses during the time period and second digital value indicative of a period of time between a first pulse and a last pulse occurring during the time period.

In accordance with another aspect of the present invention, a modular radiation detector unit for use in computerized tomographic imaging is provided. The modular radiation detector unit includes a circuit board and a plurality of x-ray sensitive cells disposed on the circuit board. The x-ray sensitive cells receive x-rays after the x-rays have passed through an examination region and generate an analog signal indicative of the x-rays received thereby. The modular radiation detector unit also includes at least one integrated circuit disposed on the circuit board. The integrated circuit includes a plurality of analog to digital conversion channels for converting the analog signals from a plurality of x-ray sensitive cells to digital data.

In accordance with a more limited aspect of the present invention, the plurality of x-ray sensitive cells are arranged in a two-dimensional array having a number of rows and a number of columns.

In accordance with a more limited aspect of the present invention, each row of the two-dimensional array corresponds to a single slice of computerized tomographic image data.

In accordance with a more limited aspect of the present invention, at least one row of the two-dimensional array of x-ray sensitive cells is connected to one integrated circuit.

In accordance with a more limited aspect of the present invention, each analog to digital conversion channel receives analog data from not more than one of the x-ray sensitive cells.

In accordance with a more limited aspect of the present invention, each channel includes a current to frequency converter for generating a number of electrical pulses during a time period. The number of pulses is proportional to the magnitude of the analog signal converted by the channel.

In accordance with a more limited aspect of the present invention, each channel also includes a frequency to digital converter which generates a first digital value indicative of the number of pulses generated during the time period and a second digital value indicative of a period of time between a first pulse and a last pulse of the time period.

In accordance with a more limited aspect of the present invention, each channel includes a parallel to serial converter which outputs the first and second digital values in a serial output stream.

In accordance with a more limited aspect of the present invention, the parallel to serial converters are interconnected to generate a serial output of the digital data of a plurality of channels.

In accordance with another aspect of the present invention, a modular radiation detector unit for use in CT imaging is provided. The modular radiation detector unit includes a circuit board, a plurality of x-ray sensitive cells disposed on the circuit board for receiving x-rays after the x-rays have passed through an examination region and for generating analog signals indicative of the x-rays received thereby, and a plurality of integrated circuits disposed on the circuit board and in electrical connection with the x-ray sensitive cells. The integrated circuits include a plurality of channels with each channel being connected with a single x-ray sensitive cell for receiving the analog signal generated by the x-ray sensitive cell and for converting the analog signal to first digital data. The modular radiation detector unit also includes means for receiving second digital data from a second modular radiation detector unit. The second digital data is indicative of the x-rays received at the second modular radiation detector unit. The modular radiation detector unit also includes means for outputting the first and second digital data to a third modular radiation detector unit.

In accordance with a more limited aspect of the present invention, each channel includes a ratiometric current to frequency converter for generating a number of electrical pulses during a time period, the number of pulses being proportional to the magnitude of the analog signal received by the channel.

In accordance with a more limited aspect of the present invention, each channel also includes a frequency to digital converter which generates a first digital value indicative of the number of pulses generated during the time period and a second digital value indicative of a period of time between a first pulse and a last pulse during the time period.

In accordance with a more limited aspect of the present invention, the modular radiation detector unit also includes means to assure that the value of the first digital value is at least two.

In accordance with a more limited aspect of the present invention, each channel also includes parallel to serial converters for outputting the digital data in a serial output stream.

In accordance with a more limited aspect of the present invention, the plurality of x-ray sensitive cells are arranged in a two-dimensional array with each row of the array corresponding to a slice of computerized tomographic image data.

In accordance with a more limited aspect of the present invention, the two dimensional array includes at least thirty-two rows and at least sixteen columns.

In accordance with a more limited aspect of the present invention, each integrated circuit includes at least thirty-two channels.

In accordance with a more limited aspect of the present invention, the integrated circuits are disposed on the circuit board so that the variability of the distances from the x-ray sensitive cells to their respective integrated circuits is minimized.

One advantage of the present invention is that it provides direct digital conversion of radiation signals detected during a CT scan.

Another advantage of the present invention is that it provides a CT system with reduced noise and fictitious data.

Another advantage of the present invention is that it provides a simpler way to convert radiation received in the examination region to digital data.

Another advantage of the present invention is that it provides a more efficient way to process data during multi-slice CT data acquisition.

Another advantage of the present invention is that it provides a simpler cabling system to be used for transferring image data from an examination region to an image processor.

Another advantage of the present invention is that it provides a CT imaging system having x-ray sensitive cells disposed on the same modular assembly as an appropriate number of integrated circuits for generating digital data indicative of the radiation received by the x-ray sensitive cells.

Another advantage of the present invention is that it provides a CT imaging system having radiation detector units whose outputs can be connected to form a single serial stream of digital data for transfer to a remote image reconstruction processor.

Still further advantages of the present invention will become apparent to those of ordinary skill in the art upon a reading and understanding of the following description of the preferred embodiments.

DRAWINGS

The invention may take form in various components and arrangements of components, and in various steps and arrangements of steps. The drawings are only for purposes of illustrating a preferred embodiment and are not to be construed as limiting the invention.

DESCRIPTION

Figure 1:
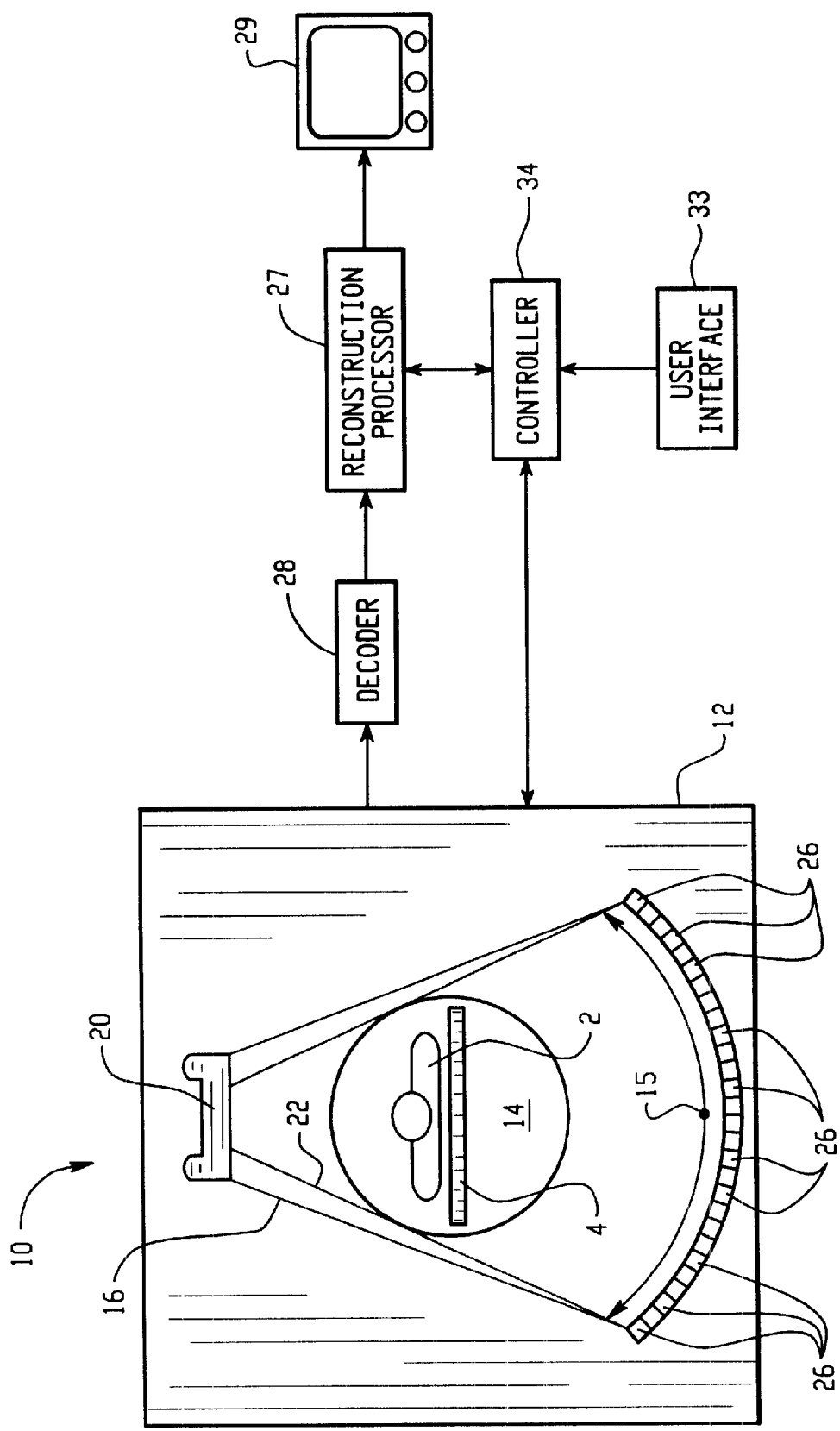
FIG. 1 is a diagrammatic illustration of a CT scanner.

With reference to FIG. 1, a CT scanner 10 selectively images regions of a patient 2 supported on a patient support 4 in an examination region 14. The CT scanner includes a stationary gantry portion 12. A rotating gantry portion 16 is mounted on the stationary gantry portion 12 for rotation about the examination region 14. An x-ray source 20, such as an x-ray tube, is arranged on the rotating gantry portion 16 such that a beam of radiation 22 passes through the examination region 14 as the rotating gantry portion 16 rotates.

In a multislice CT scanner, the beam of radiation 22 is a cone or fan-shaped beam which passes through a plurality of longitudinal slices of the patient 2. In a single slice CT scanner, the beam of radiation 22 is a relatively thinner fan-shaped beam for irradiating a single slice of the patient 2. As the x-ray source 20 rotates about the examination region 14, the patient support 4 is moved longitudinally so that the patient 2 is irradiated is a spiral or helical pattern. Alternately, the patient support 4 may be moved in a succession of discrete longitudinal steps.

In the illustrated third generation CT scanner, a plurality of radiation detectors 26 are mounted on the rotating gantry portion 16 on a side of the examination region 14 opposite the x-ray source 20 such that they span the arc 15 defined by the beam of radiation 22. Each detector is sampled a multiplicity of times as the x-ray source 20 rotates around the examination region 14.

Alternately, the radiation detectors 26 may be mounted in a fourth generation CT scanner, a baggage inspection device, or other configuration in which detectors are stationary. In a fourth generation scanner configuration, the radiation detectors 26 are mounted peripherally around the examination region 14 on the stationary gantry portion 12. An arc of detectors which span the radiation emanating from the x-ray source 20 are sampled concurrently at short time intervals as the x-ray source 20 rotates around the examination region 14.

Regardless of the configuration, the radiation detectors 26 are arranged to receive the x-ray radiation emitted from the x-ray source 20 after the radiation has traversed the examination region 14.

Each of the radiation detectors 26 produces an output signal which is a function of an intensity of received radiation. Sampled data from the radiation detectors 26 are digitized and transferred to a decoder 28 such as a serial to parallel converter. In the case of a third generation scanner, the data are transferred from the rotating radiation detectors 26 to the decoder 28 which is typically stationary.

The serial to parallel converter 28 converts the data from the radiation detectors from serial to parallel form. An image reconstruction processor 27 reconstructs this into one or more human-readable images of the object being imaged. Data from the image reconstruction processor 27 are then sent to an output device 29 such as an image processor, a video monitor, film, or other storage medium.

A user interface 33 such as a keyboard, mouse, or other input device is provided to allow a user to adjust desired scan parameters, such as x-ray tube voltage, mAS, gantry rotation speed, as well as other operating parameters of the CT scanner. The user interface 33 is connected to a controller 34. The controller 34 is connected to the CT scanner 10 and image reconstruction processor 27 so that information can be passed back and forth between those components.

Figure 2:
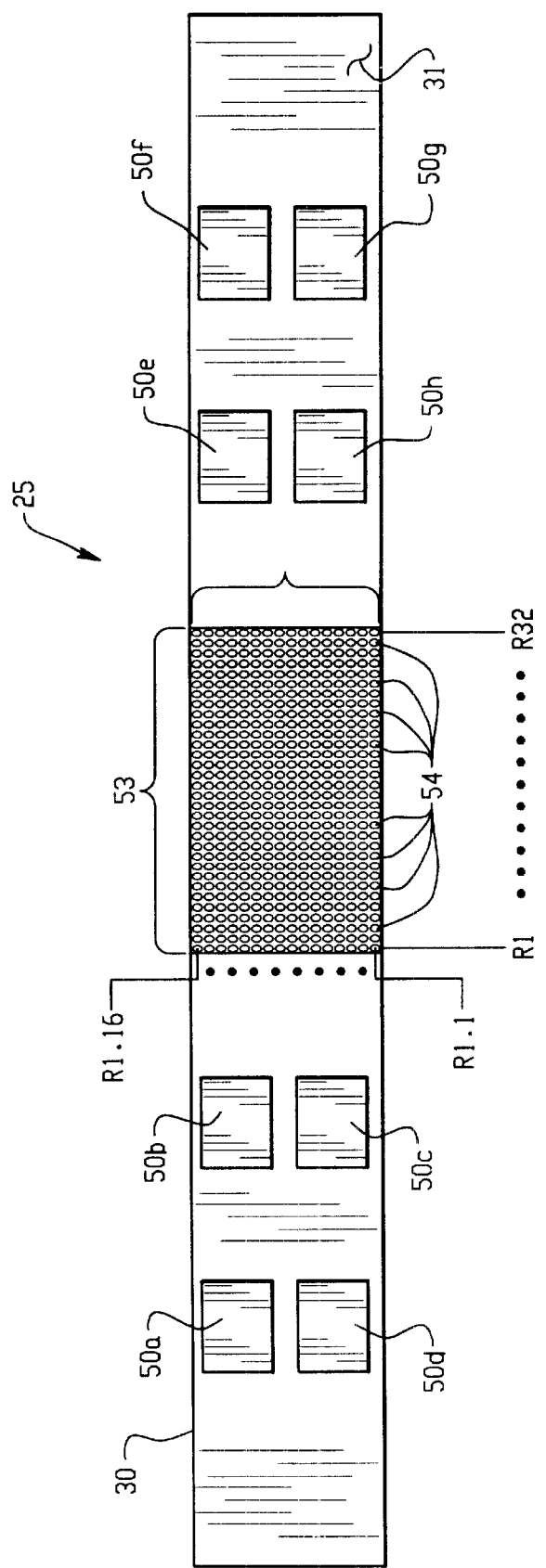
FIG. 2 is a diagram of a radiation detector unit.

Continuing with FIG. 1 and with particular reference to FIG. 2, the radiation detectors 26 will be described in greater detail. In a third generation scanner, a plurality of radiation detector units 25 are disposed so as to span the arc 15 defined by the radiation beam 22. The radiation detector units 25 are mounted side-by-side with their long axes parallel to the longitudinal axis of the scanner.

Each radiation detector unit 25 includes a multi-layer circuit board 30, an array 53 of x-ray sensitive cells 54, and a plurality of mixed signal integrated circuits 50 together with ancillary support electronics. Each radiation sensitive cell 54 includes a scintillator and photodiode which generates a low-level analog electrical current, for example a current in the range of 0–2 microamperes full scale, which is a function of the intensity of the radiation received thereby. In the embodiment shown, there are thirty-two (32) rows, R1–R32, of x-ray sensitive cells 54, thereby defining a thirty-two (32) slice scanner. Each row comprises sixteen (16) cells 54. The cells of row R1 are labeled R1.1–R1.16 and succeeding rows are labeled accordingly. Other numbers of rows and columns can be implemented, for example two rows of sixteen cells per row in a two-slice embodiment. Each circuit board 30 includes sixteen integrated circuits, with eight being mounted on the top side 31 of the circuit board 30 and eight being mounted on the bottom side (not shown.)

Figure 3:
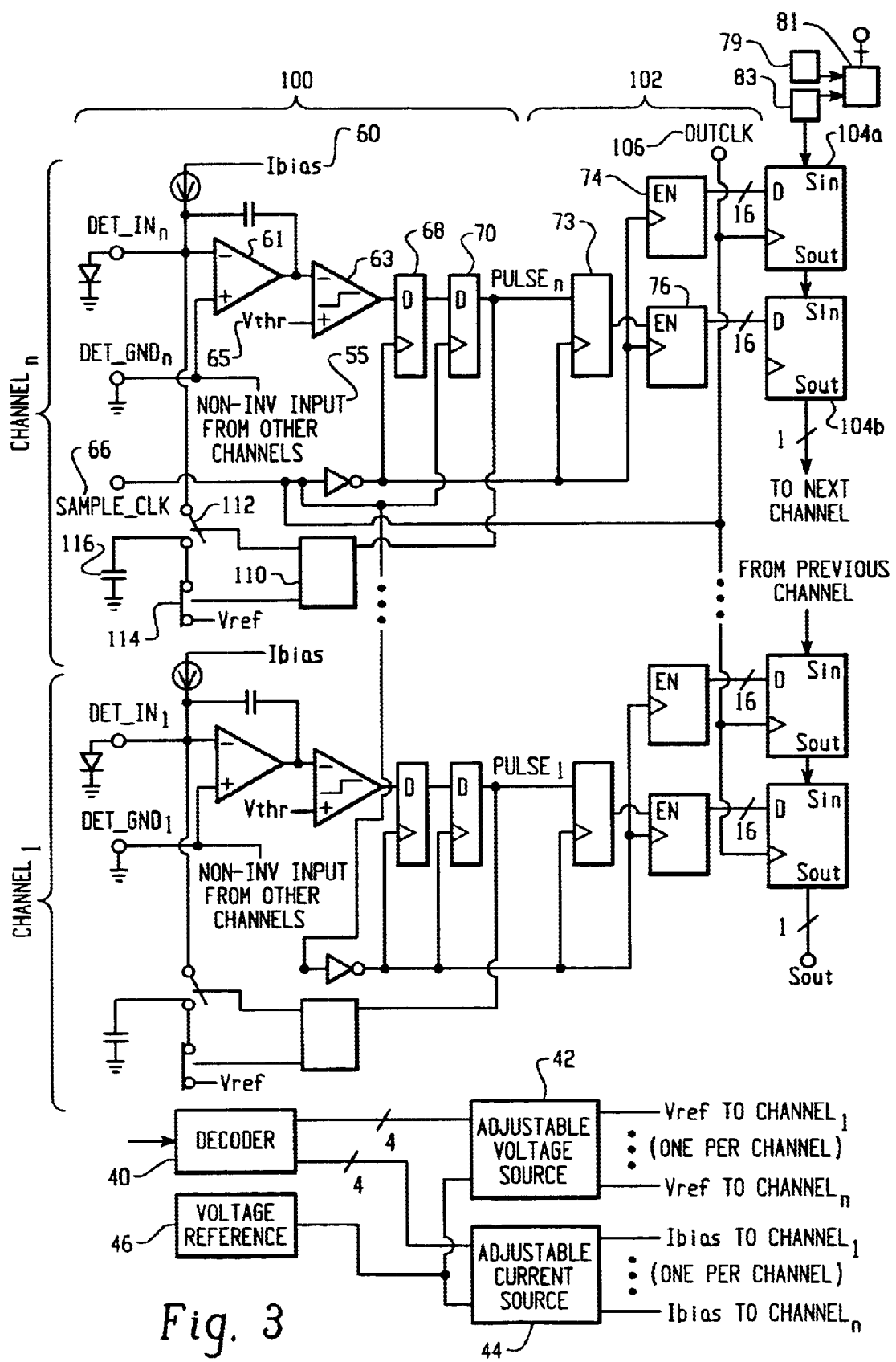
FIG. 3 is a system-level block diagram of an integrated circuit.

The integrated circuits 50 function as analog to digital converters which receive the electrical signals generated by the x-ray sensitive cells 54 and generate digital data values indicative thereof. Turning now to FIG. 3, each channel of the integrated circuit 50 includes a ratiometric current to frequency converter 100 which generates a pulse train whose frequency is proportional to the input current. Each channel of the integrated circuit 50 also includes a frequency to digital converter 102 which generates digital data indicative of the frequency of the pulse train, and a parallel to series converter 104 which converts digital data to serial form. While the use of a ratiometric current to frequency converter is described herein, other analog to digital conversion techniques could be used provided that they meet desired dynamic range, accuracy, and speed requirements. A particular advantage of the current to frequency technique, however, is its inherent linearity and ease of implementation on a single application specific integrated circuit.

Figure 4:
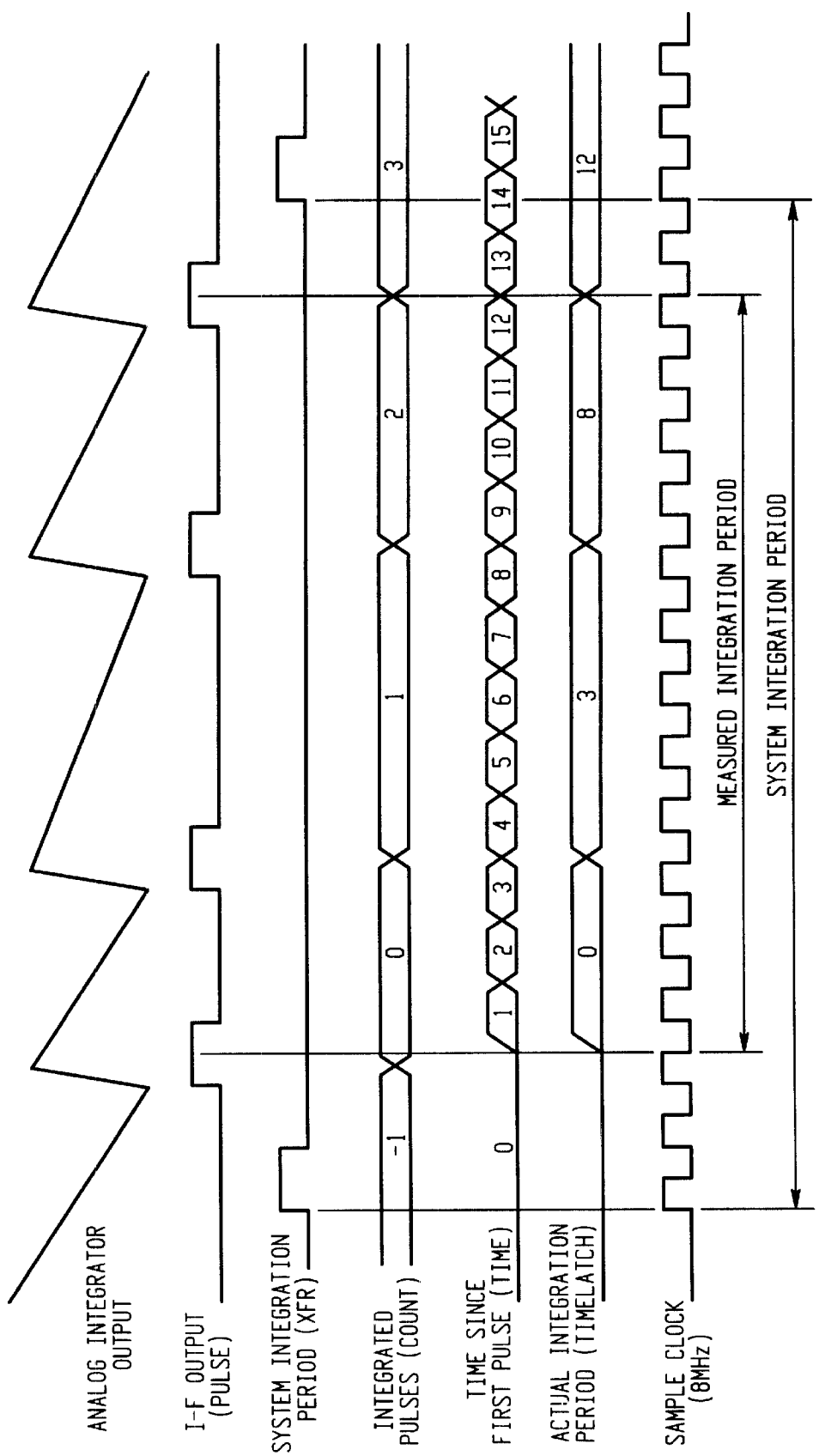
FIG. 4 is a system level timing diagram of an integrated circuit.

Continuing with FIG. 3 and with additional reference to FIG. 4 the current to frequency converter 100 includes a current source 60, an integrator 61, a comparator 63, a clock 66, and two flip-flops 68, 70. One of the x-ray sensitive cells 54 serves as input to the inverting pin of the integrator 61. A current source 55 is also connected to the non-inverting integrator pin. The output of the integrator 61 is fed into the comparator 63 which generates a pulse when the integrator output exceeds a threshold 65 of the comparator 63. The pulse also resets the integrator 61 to begin another integrator cycle. The pulse train produced by the comparator 63 is synchronized, using two flip-flops 68, 70, to a clock 66 and is sent to the frequency to digital converter 102. In one embodiment, the frequency of the clock 66 is 8 MHz.

The output pulse is also provided to an integrator reset circuit which includes a non-overlapping controller 110, a pair of switches 112, 114, and a reset capacitor 116. The non-overlapping controller causes switch 112 to open before switch 114 is closed, and vice versa. Upon the occurrence of each pulse, a current of opposite direction to that of the integrator's 61 input current is applied to the non-inverting input of the integrator 61.

As described above, a bias offset current $I_{bias}$ and reference voltage $V_{ref}$ is applied to each channel. A decoder 40 receives serial data from the controller 34 indicative of the desired current and voltage values. This data is converted to parallel form and provided to adjustable current 44 and voltage 42 sources, for example as 4 bit data words. A stable voltage reference 46 provides a reference input to the current 44 and voltage 42 sources. Alternately, the current source may be implemented using a current mirror circuit supplied by an external current source. The voltage reference 46 may be implemented on chip or alternately external to the integrated circuit 50.

The resultant pulse train is sent to the frequency to digital converter 102, which includes a pulse detector 73, a pulse counter 74, and a time counter and latch 76. The pulse counter 74 and time counter and latch 76 are preferably 16-bit devices, although other numbers of bits may be implemented. With particular reference to FIG. 4, the pulse counter 74 is incremented upon the occurrence of each pulse in the pulse train to generate a digital value referred to as COUNT.

The pulse detector 73 enables the time counter 76 upon the occurrence of the first pulse in a given system integration period so that the time counter is incremented with each pulse of the system clock 66. The time counter 76 thereby generates a digital value referred to as TIME which is indicative of the elapsed time since the first pulse of the system integration period. The system integration period is preferably determined by system controller 34 and provided via control lines as an input to decoder 40 so that the system integration period may be adjusted.

The latch portion of the time counter and latch 76 latches the then-current TIME value upon the occurrence of each pulse to generate a digital value referred to as TIMELATCH. Thus, the TIMELATCH value is indicative of the elapsed time between the first and last pulses in a given system integration period. The ratio of COUNT to TIMELATCH is indicative of the frequency of the pulse train, and hence the value of the current generated by the x-ray sensitive cell 54. The pulse counter 74 and time counter and latch 76 are reset upon completion of each system integration period. The calculation of the ratio of COUNT to TIMELATCH is performed externally from the integrated circuit 50. Alternately, the integrated circuit 50 could be modified to perform such calculation.

The bias current $I_{bias}$ provided to the inverting input of each integrator 61 is selected so that during any system integration period, even in the absence of radiation being incident on the x-ray sensitive cell 54, there are at least two pulses in the pulse train. The reference voltage $V_{ref}$ applied to the reset capacitor 116 is selected so that the charge applied to the inverting input of the integrator is twice the integrator's full scale input magnitude. Hence, the full scale input of the integrator is a function of the reference voltage Vref.

Returning now to FIG. 3, the COUNT and TIMELATCH values are provided to parallel to serial converters 104 such as shift registers. An output clock signal 106 causes the corresponding values to be shifted through the shift registers to provide a serial output stream. The parallel to serial converters 104 are double buffered so that the clocking of the serial output stream and the analog to digital conversion processes may occur concurrently.

While the foregoing discussion has focused on the operation of a single channel, it will be appreciated that the integrated circuit 50 may likewise include additional such channels for processing the signals from each of a plurality of x-ray sensitive cells 54. In the embodiment shown in FIG. 3 each integrated circuit may contain thirty two (32) channels, although different numbers of channels may be implemented. The inputs and outputs of the parallel to serial converter 104 for each channel may be interconnected so that the serial data from one channel feeds the parallel to serial converter 104 for a successive channel. Hence, data indicative of a plurality of channels may be combined to form a single output stream. Moreover, the process may be repeated so that the data from a plurality of integrated circuits 50 are combined to form a single output chain.

The integrated circuit 50 also contains a control register 79, which contains status bits indicative of the operation and status of the integrated circuit 50, and an associated control parallel to serial converter 81 such as a shift register. An error detection processor 83 such as a parity generator generates a parity bit indicative of the parity of the integrated circuit's output data. Odd parity is preferably selected so that a loss of power or communications may be more readily detected. In one embodiment, the number of status bits plus parity information is equal to the number of bits associated with each channel, for example thirty-two (32), although other numbers of status and error information bits may be implemented. In any event, the output of the control parallel to serial converter 81 feeds the parallel to serial converter for one of the channels.

Figure 5A:
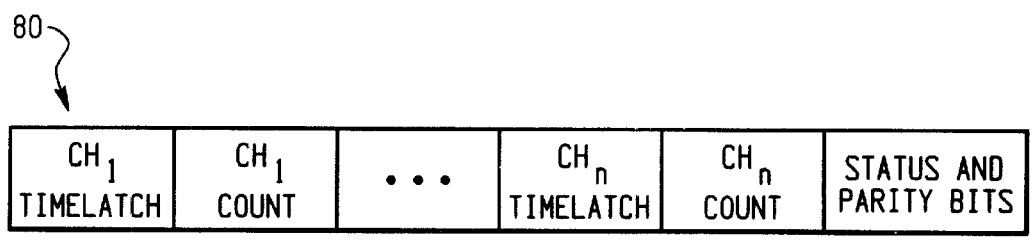
FIG. 5A is a diagram of the output serial line data of an integrated circuit.

With particular reference to FIG. 5A, the output serial chain 80 from each integrated circuit 50 includes data for each of its associated x-ray sensitive cells 54. In the embodiment shown, there are thirty-two pairs of COUNT and TIMELATCH words and thirty-two status and parity bits. Therefore, in the case where the COUNT and TIMELATCH words are each 16-bits long, the output serial chain of a single integrated circuit 50 comprises a one-bit serial stream of 1056 bits. As noted earlier, the integrated circuit 50 can comprise varying numbers of channels other than thirty-two. Regardless of the number of channels, the input from the channels can be parallel processed and output, along with associated status and parity bits, in a serial chain.

Figure 5B:
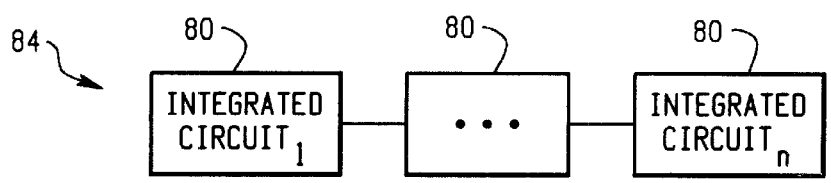
FIG. 5B is a diagram of the output serial line data of multiple integrated circuits.

Referring to FIG. 5B, the outputs of the serial to parallel converters 104 for each integrated circuit 50 are interconnected with those of the other integrated circuits 50 disposed on the radiation detector unit 25 so that the serial data from one integrated circuit 50 feeds the parallel to serial converter 104 for a successive integrated circuit 50. Thus, output serial chains 80 from each integrated circuit 50 on a radiation detector 26 may be serially combined to form a multiple integrated circuit data stream 84.

In one embodiment, four such integrated circuits 50 are connected (i.e. n=4 in FIG. 5B with a serial output clock rate of 24 MHz.

Figure 5C:
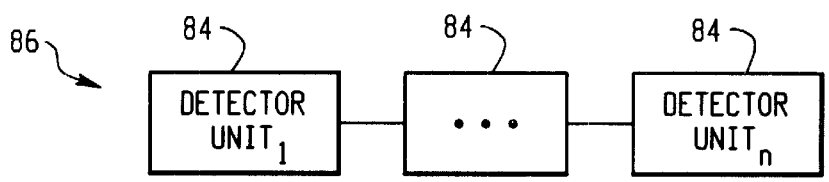
FIG. 5C is a diagram of the output serial line data of multiple radiation detectors.

With reference to FIG. 5C, the outputs from each radiation detector unit 25 are interconnected with those of the other radiation detector units 25 so that the serial data from one radiation detector unit 25 feeds a successive radiation detector 25. Thus, serial data from each radiation detector 25 may be combined into a multiple detector data stream 86 comprising a serial chain of digital data from multiple radiation detector units 25.

Figure 5D:
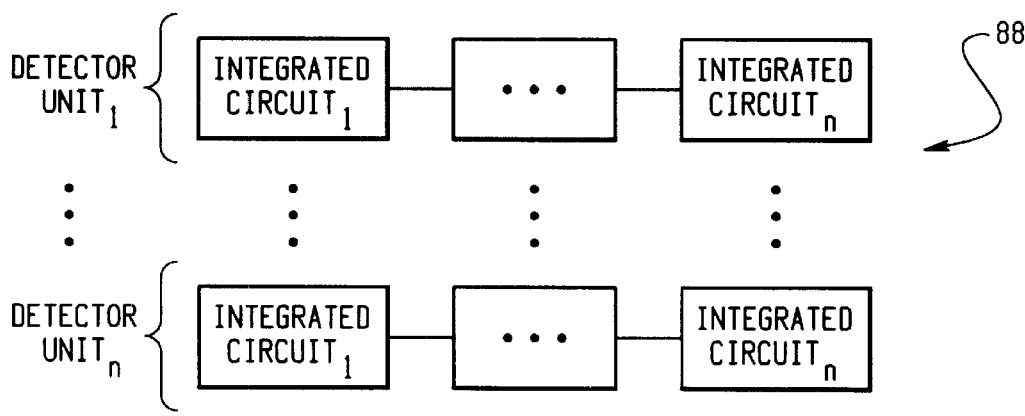
FIG. 5D is a diagram of the output parallel data of multiple radiation detectors.

With reference to FIG. 5D, multiple integrated circuit data streams 84 may be combined in parallel on the radiation detector units 25 to form parallel multiple detector data paths 88 in order to facilitate modularity to support a variety of system configurations.

The output chain comprising data from the radiation detector units 25 is transmitted along a serial line to the image reconstruction processor 27 where the serial data are parsed into parallel format at the serial to parallel processor 28 and an image indicative of the patient 2 in the examination region 14 is processed. Subsequent image data can then be displayed and/or stored on the output device 29 for subsequent analysis. Alternate embodiments may include transmitting the digital data from individual radiation detectors 26 in parallel to the image reconstruction processor 27 and may also include transmitting the digital data from individual integrated circuits 50 in parallel to the image reconstruction processor 27.

Figure 6A:
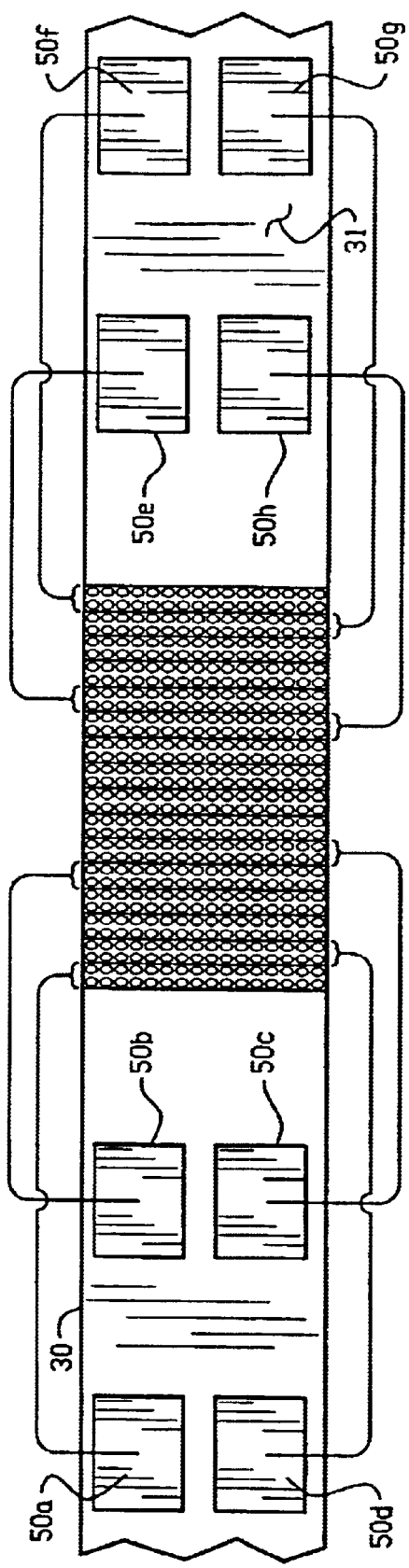
FIG. 6A is a diagrammatic illustration of x-ray sensitive cells of a radiation detector unit being connected to integrated circuits.
Figure 6B:
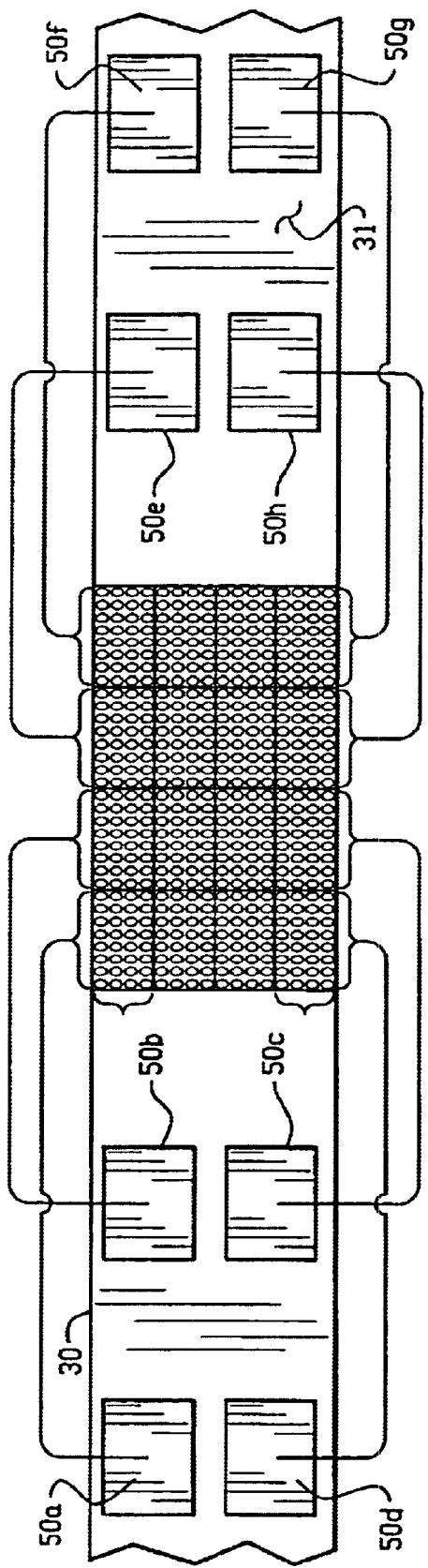
FIG. 6B is a diagrammatic illustration of x-ray sensitive cells of a radiation detector unit being connected to an integrated circuit.

Connections of individual x-ray sensitive cells 54 to the integrated circuits 50 are shown in FIGS. 6A and 6B. In the embodiment shown in FIG. 6B, blocks of cells, e.g. R1.1 . . . R1.4, R8.1 . . . R8.4 are each connected to separate integrated circuits 50a, 50b, etc. In such an embodiment, the blocks and integrated circuits 50a, 50b, 50c, etc. are preferably interleaved so as to minimize variations in the distance between the blocks of cells and their respective integrated circuits 50. Thus, for example, the left most blocks of cells are connected to the left most integrated circuits 50a, 50d, and so on. It will be appreciated that blocks of cells not shown to be connected in FIG. 6b are connected to corresponding integrated circuits 50 disposed on the other side of the circuit board 30.

In an alternate embodiment shown in FIG. 6A, pairs of rows, e.g. rows R1 and R2, are each connected to a single integrated circuit 50. Again, the rows and integrated circuits 50a, 50b, 50c, etc. are preferably interleaved so as to minimize variations in the distance between the rows of cells and their respective integrated circuits 50. Thus, for example, the left most blocks of cells are connected to the left most integrated circuits 50a, 50d, and so on. It will be appreciated that blocks of cells not shown to be connected in FIG. 6b are connected to corresponding integrated circuits 50 disposed on the other side of the circuit board 30. One advantage to this embodiment is that each row of cells is processed within a single integrated circuit 50. Such a configuration reduces the likelihood of variations in the processing of each row of cells, which variations can lead to artifacts, particularly in third generation scanners.

The invention has been described with reference to the preferred embodiment. Obviously, modifications and alterations will occur to others upon reading and understanding the preceding description. It is intended that the invention be construed as including all such modifications and alterations insofar as they come within the scope of the appended claims or the equivalents thereof.

What is claimed is:

1. A computerized tomographic imaging system comprising:
    a stationary gantry portion defining an examination region;
    a rotating gantry portion for rotation about the examination region;
    an x-ray source disposed on the rotating gantry portion for projecting x-rays through the examination region; and
    a plurality of modular radiation detector units disposed across the examination region from the x-ray source, each radiation detector unit comprising:
        an array of x-ray sensitive cells for receiving radiation from the x-ray source after it has passed through the examination region and for generating an analog signal indicative of the radiation received thereby; and
        a plurality of integrated circuits connected to the x-ray sensitive cells, each integrated circuit comprising a plurality of channels, each channel receiving the analog signal from an x-ray sensitive cell and generating digital data indicative of the value of the analog signal.

2. A computerized tomographic imaging system according to claim 1 wherein each modular radiation detector unit further comprises a circuit board, the plurality of x-ray sensitive cells and plurality of integrated circuits being disposed on the circuit board.

3. A computerized tomographic imaging system according to claim 2 wherein the integrated circuits are disposed on the circuit board so that the variability of the distances from the x-ray sensitive cells to their respective integrated circuits is minimized.

4. A computerized tomographic imaging system according to claim 1 wherein each integrated circuit comprises at least thirty-two channels.

5. A computerized tomographic imaging system according to claim 1 wherein each channel comprises a ratiometric current to frequency converter which generates a number of electrical pulses during a time period, the number of pulses being proportional to the magnitude of the analog signal.

6. A computerized tomographic imaging system according to claim 5 wherein each channel further comprises a frequency to digital converter which generates a first digital value indicative of the number of pulses generated during the time period and a second digital value indicative of a period of time between a first pulse and a last pulse of the time period.

7. A computerized tomographic imaging system according to claim 1 wherein each channel comprises a parallel to serial converter, the parallel to serial converter including means for interconnecting the channels so that the digital data from a plurality of the channels are combined to form a single output stream of digital data.

8. A computerized tomographic imaging system according to claim 1 wherein the array of x-ray sensitive cells is an array having M rows and N columns, M and N being integers greater than or equal to two.

9. A computerized tomographic imaging system according to claim 8 wherein each row of the array of x-ray sensitive cells corresponds to a single slice of image data.

10. A computerized tomographic imaging system according to claim 8 wherein at least one row of x-ray sensitive cells is connected to one of the integrated circuits.

11. A CT imaging system comprising:
    a gantry defining an examination region;
    an x-ray source for projecting x-rays through the examination region;
    a plurality of x-ray sensitive cells for converting x-rays that pass through the examination region into a plurality of analog signals; and
    a plurality of integrated circuits in electrical connection with the x-ray sensitive cells, each integrated circuit receiving the analog signals and generating digital data indicative of the values of the analog signals, the integrated circuits being disposed at the perimeter of the examination region and comprising means for interconnecting the integrated circuits so that the digital data from a plurality of the integrated circuits are combined to form a single output stream of digital data.

12. A CT imaging system according to claim 11 wherein each integrated circuit further comprises a plurality of channels, each channel comprising an analog to digital converter for converting the analog signal of a single x-ray sensitive cell to digital data.

13. A CT imaging system according to claim 12 wherein each channel further comprises a ratiometric current to frequency converter for generating a number of electrical pulses during a time period, the number of pulses being proportional to the magnitude of the analog signal.

14. A CT imaging system according to claim 13 wherein each channel further comprises a frequency to digital converter which generates a first digital value indicative of the number of pulses generated during the time period and a second digital value indicative of a period of time between a first pulse and a last pulse of the time period.

15. A CT imaging system according to claim 14 further comprising means to assure that the value of the first digital value is at least two.

16. A CT imaging system according to claim 12 wherein each channel further comprises a parallel to serial converter for outputting the digital data in a serial output stream.

17. A CT imaging system according to claim 11 further comprising a plurality of circuit boards disposed at the perimeter of the examination region, the x-ray sensitive cells and the integrated circuits being disposed on the circuit boards.

18. A CT imaging system comprising:
    a stationary gantry portion;
    a rotating gantry portion for rotation about an examination region;
    an x-ray source disposed on the rotating gantry portion for projecting x-rays through the examination region;
    a plurality of x-ray sensitive cells disposed across the examination region from the x-ray source for receiving x-rays originating at the x-ray source and generating analog signals indicative of the x-rays received thereby; and
    at least one integrated circuit disposed across the examination region from the x-ray source, the at least one integrated circuit comprising a plurality of channels, each channel coupled to a single x-ray sensitive cell for receiving the analog signal from the cell and for generating digital data indicative of the value of the analog signal.

19. A CT imaging system according to claim 18 wherein the plurality of x-ray sensitive cells and the at least one integrated circuit are disposed on a circuit board.

20. A CT imaging system according to claim 19 wherein the plurality of x-ray sensitive cells are arranged in a two-dimensional array.

21. A CT imaging system according to claim 20 wherein the two-dimensional array comprises at least two rows and at least two columns of x-ray sensitive cells.

22. A computerized tomographic imaging system according to claim 18 wherein each channel comprises a ratiometric current to frequency converter which generates a number of electrical pulses during a time period, the number of pulses being proportional to the magnitude of the analog signal received by the channel.

23. A computerized tomographic imaging system according to claim 22 wherein each channel further comprises a frequency to digital converter which generates a first digital value indicative of the number of pulses generated during the time period and a second digital value indicative of a period of time between a first pulse and a last pulse of the time period.

24. A computerized tomographic imaging system according to claim 18 wherein each channel comprises a parallel to serial converter for outputting the digital data of a plurality of x-ray sensitive cells in a serial output stream.

25. A CT imaging system according to claim 18, the at least one integrated circuit further comprising means for receiving digital data from a second integrated circuit, the received digital data indicative of the values of the analog signals of the second integrated circuit and means for sending digital data to a third integrated circuit, the sent digital data being indicative of the values of the analog signals of the at least one integrated circuit.

26. A computerized tomographic imaging system comprising:
    a stationary gantry portion having an examination region;
    a rotating gantry portion for rotation about the examination region;
    an x-ray source mounted to the rotating gantry portion for projecting x-rays through the examination region; and
    a plurality of radiation detector units disposed across the examination region from the x-ray source, each radiation detector unit comprising:
        a circuit board;
        x-ray detector means for generating analog signals indicative of radiation that passes from the x-ray source to the radiation detector unit, said means for generating analog signals comprising a two dimensional array of x-ray sensitive cells and being disposed on the circuit board; and
        multi-channel analog to digital conversion means for converting the analog signals to digital data, each channel of the multi-channel analog to digital conversion means connected to a single x-ray sensitive cell, said multi-channel analog to digital conversion means being disposed on the circuit board.

27. A computerized tomographic imaging system according to claim 26 wherein each channel comprises a ratiometric current to frequency converter for generating a number of electrical pulses during a time period, the number of pulses being proportional to the magnitude of the analog signal.

28. A computerized tomographic imaging system according to claim 27 wherein each channel further comprises a frequency to digital converter which generates a first digital value indicative of the number of pulses generated during the time period and a second digital value indicative of a period of time between a first pulse and a last pulse of the time period.

29. A computerized tomographic imaging system according to claim 26 wherein each channel comprises a parallel to serial converter for outputting the digital data of the two-dimensional array of x-ray sensitive cells in a serial output stream.

30. A computerized tomographic imaging system according to claim 26 wherein each array of x-ray sensitive cells comprises a number of rows and a number of columns and each row corresponds to a single slice of image data.

31. A computerized tomographic imaging system according to claim 30 wherein the multi-channel analog to digital conversion means comprises at least one integrated circuit and the x-ray sensitive cells of one row of the array of x-ray sensitive cells are connected to the same integrated circuit.

32. A method of computerized tomographic imaging comprising:
    projecting x-rays through an examination region using an x-ray source;
    detecting the projected x-rays after they have crossed the examination region using a plurality of x-ray sensitive cells disposed on a circuit board, the plurality of x-ray sensitive cells each generating a corresponding analog signal indicative of the x-rays detected thereby; and
    converting the analog signals to digital data using at least one integrated circuit, the integrated circuit comprising multiple channels for analog to digital conversion of the analog signals and being disposed on the circuit board, each channel converting the analog signal of a single x-ray sensitive cell.

33. A method of medical imaging according to claim 32 further comprising the step of generating a serial data stream comprising the digital data from a plurality of x-ray sensitive cells, the step of generating a serial data stream being performed using the at least one integrated circuit.

34. A method of medical imaging according to claim 32 wherein the step of converting the analog signals to digital data comprises, for each x-ray sensitive cell:
storing a first value representing a number of pulses during a time period, the pulses occurring when the analog signal from each cell reaches a threshold value; and
storing a second value indicative of the time between a first pulse and a last pulse that occur during the time period.

35. A method of medical imaging according to claim 34 further comprising the step of assuring that at least two pulses occur during the time period.

36. A method of CT imaging comprising:
rotating an x-ray source about an examination region;
projecting x-rays through the examination region using the x-ray source;
detecting the projected x-rays using a plurality of two-dimensional arrays of x-ray sensitive cells, the arrays of x-ray sensitive cells being disposed on a plurality of circuit boards, each x-ray sensitive cell generating an analog signal indicative of the x-rays detected by said cell; and
generating digital signals indicative of the analog signals using a plurality of integrated circuits, the integrated circuits being disposed on the circuit boards and each integrated circuit comprising a plurality of channels, each channel converting to digital the analog signal from not more than one x-ray sensitive cell.

37. A method of CT imaging according to claim 36 further comprising the step of generating a single output stream of the digital data by interconnecting the channels of the integrated circuits.

38. A method of CT imaging according to claim 36 wherein each channel of the integrated circuits comprises a ratiometric current to frequency converter.

39. A method of CT imaging according to claim 38 wherein each channel further comprises a frequency to digital converter for generating a number of electrical pulses during a time period, the number of pulses being proportional to the magnitude of the analog signal.

40. A method of CT imaging according to claim 39 further comprising generating a first digital value indicative of a number of electrical pulses during the time period and second digital value indicative of a period of time between a first pulse and a last pulse occurring during the time period.

41. A modular radiation detector unit for use in computerized tomographic imaging comprising:
a circuit board;
a plurality of x-ray sensitive cells disposed on the circuit board, the x-ray sensitive cells for receiving x-rays after the x-rays have passed through an examination region and generating an analog signal indicative of the x-rays received thereby; and
at least one integrated circuit disposed on the circuit board, the integrated circuit comprising a plurality of analog to digital conversion channels for converting the analog signals from a plurality of x-ray sensitive cells to digital data.

42. A modular radiation detector unit according to claim 41 wherein the plurality of x-ray sensitive cells are arranged in a two-dimensional array having a number of rows and a number of columns.

43. A modular radiation detector unit according to claim 42 wherein each row of the two-dimensional array corresponds to a single slice of computerized tomographic image data.

44. A modular radiation detector unit according to claim 43 wherein at least one row of the two-dimensional array of x-ray sensitive cells is connected to one integrated circuit.

45. A modular radiation detector unit according to claim 41 wherein each analog to digital conversion channel receives analog data from not more than one of the x-ray sensitive cells.

46. A modular radiation detector unit according to claim 41 wherein each channel comprises a current to frequency converter for generating a number of electrical pulses during a time period, the number of pulses being proportional to the magnitude of the analog signal converted by said channel.

47. A modular radiation detector unit according to claim 46 wherein each channel further comprises a frequency to digital converter which generates a first digital value indicative of the number of pulses generated during the time period and a second digital value indicative of a period of time between a first pulse and a last pulse of the time period.

48. A modular radiation detector unit according to claim 47 wherein each channel comprises a parallel to serial converter which outputs the first and second digital values in a serial output stream.

49. A modular radiation detector unit according to claim 48 wherein the parallel to serial converters are interconnected to generate a serial output of the digital data of a plurality of channels.

50. A modular radiation detector unit for use in CT imaging comprising:
a circuit board;
a plurality of x-ray sensitive cells disposed on the circuit board for receiving x-rays after the x-rays have passed through an examination region and for generating analog signals indicative of the x-rays received thereby;
a plurality of integrated circuits disposed on the circuit board and in electrical connection with the x-ray sensitive cells, comprising a plurality of channels, each channel being connected with a single x-ray sensitive cell for receiving the analog signal generated by the x-ray sensitive cell and for converting the analog signal to first digital data;
means for receiving second digital data from a second modular radiation detector unit, the second digital data being indicative of the x-rays received at the second modular radiation detector unit; and
means for outputting the first and second digital data to a third modular radiation detector unit.

51. A modular radiation detector unit according to claim 50 wherein each channel comprises a ratiometric current to frequency converter for generating a number of electrical pulses during a time period, the number of pulses being proportional to the magnitude of the analog signal received by the channel.

52. A modular radiation detector unit according to claim 51 wherein each channel further comprises a frequency to digital converter which generates a first digital value indicative of the number of pulses generated during the time period and a second digital value indicative of a period of time between a first pulse and a last pulse during the time period.

53. A modular radiation detector unit according to claim 52 further comprising means to assure that the value of the first digital value is at least two.

54. A modular radiation detector unit according to claim 53 wherein each channel further comprises parallel to serial converters for outputting the digital data in a serial output stream.

55. A modular radiation detector unit according to claim 50 wherein the plurality of x-ray sensitive cells are arranged in a two-dimensional array with each row of the array corresponding to a slice of computerized tomographic image data.

56. A modular radiation detector unit according to claim 55 wherein the two dimensional array comprises at least thirty-two rows and at least sixteen columns.

57. A modular radiation detector unit according to claim 50 wherein each integrated circuit comprises at least thirty-two channels.

58. A modular radiation detector unit according to claim 51 wherein the integrated circuits are disposed on the circuit board so that the variability of the distances from the x-ray sensitive cells to their respective integrated circuits is minimized.

59. A modular radiation detector unit comprising:
a plurality of x-ray sensitive cells for receiving x-ray after the x-ray have passed through an examination region and for generating an output of analog signals indicative thereof; and
a plurality of integrated circuits for converting the analog signals to digital data and for combining the digital data into a serial line of digital data representing the output of the plurality of x-ray sensitive cells.

60. A computerized tomographic imaging system comprising:
a stationary gantry portion defining an examination region;
a rotating gantry portion for rotation about the examination region;
an x-ray source disposed on the rotating gantry portion for projecting x-rays through the examination region; and
a plurality of radiation detector units disposed across the examination region from the x-ray source, each radiation detector unit comprising:
an array of x-ray sensitive cells for receiving radiation from the x-ray source after it has passed through the examination region and for generating an analog signal indicative of the radiation received thereby; and
a plurality of integrated circuits connected to the x-ray sensitive cells, each integrated circuit comprising a plurality of channels, each channel receiving the analog signal from an x-ray sensitive cell and generating digital data indicative of the value of the analog signal,
wherein each channel comprises a ratiometric current to frequency converter which generates a number of electrical pulses during a time period, the number of pulses being proportional to the magnitude of the analog signal; and
each channel further comprises a frequency to digital converter which generates a first digital value indicative of the number of pulses generated during the time period and a second digital value indicative of a period of time between a first pulse and a second pulse of the time period.

61. A CT imaging system comprising:
a gantry defining an examination region;
an x-ray source for projecting x-rays through the examination region;
a plurality of x-ray sensitive cells for converting x-rays that pass through the examination region into a plurality of analog signals; and a plurality of integrated circuits in electrical connection with the x-ray sensitive cells, each integrated circuit receiving the analog signals and generating digital data indicative of the values of the analog signals, the integrated circuits being disposed at the perimeter of the examination region and comprising means for interconnecting the integrated circuits so that the digital data from a plurality of the integrated circuits are combined to form a single output stream of digital data, wherein each integrated circuit further comprises a plurality of channels, each channel comprising:
a ratiometric current to frequency converter for generating a number of electrical pulses during a time period, the number of pulses being proportional to the magnitude of the analog signal; and
a frequency to digital converter for generating a first digital value indicative of the number of pulses generated during the time period and a second digital value indicative of a period of time between a first pulse and a second pulse of the time period.

62. A CT imaging system according to claim 61 further comprising means to assure that the value of the first digital value is at least two.

63. A CT imaging system comprising:
a stationary gantry portion;
a rotating gantry portion for rotation about an examination region;
an x-ray source disposed on the rotating gantry portion for projecting x-rays through the examination region;
a plurality of x-ray sensitive cells disposed across the examination region from the x-ray source for receiving x-rays originating at the x-ray source and generating analog signals indicative of the x-rays received thereby; and
at least one integrated circuit disposed across the examination region from the x-ray source, the at least one integrated circuit comprising a plurality of channels, each channel coupled to a single x-ray sensitive cell for receiving the analog signal from the cell and for generating digital data indicative of the value of the analog signal, wherein each channel comprises:
a ratiometric current to frequency converter for generating a number of electrical pulses during a time period, the number of pulses being proportional to the magnitude of the analog signal received by the channel; and
a frequency to digital converter for generating a first digital value indicative of the number of pulses generated during the time period and a second digital value indicative of a period of time between two pulses of the time period.

64. A computerized tomographic imaging system comprising:
a stationary gantry portion having an examination region;
a rotating gantry portion for rotation about the examination region;
an x-ray source mounted to the rotating gantry portion for projecting x-rays through the examination region; and
a plurality of radiation detector units disposed across the examination region from the x-ray source, each radiation detector unit comprising:
a circuit board;
x-ray detector means for generating analog signals indicative of radiation that passes from the x-ray source to the radiation detector unit; and
multi-channel analog to digital conversion means for converting the analog signals to digital data, wherein each channel comprises:

a current to frequency converter for generating a number of electrical pulses during a time period, the number of pulses being proportional to the magnitude of the analog signal; and a frequency to digital converter for generating a first digital value indicative of the number of pulses generated during the time period and a second digital value indicative of a period of time between two pulses of the time period.

65. A method of computerized tomographic imaging comprising:

projecting x-rays through an examination region using an x-ray source;

detecting the projected x-rays after they have crossed the examination region using a plurality of x-ray sensitive cells disposed on a circuit board, the plurality of x-ray sensitive cells each generating a corresponding analog signal indicative of the x-rays detected thereby; and converting the analog signals to digital data using at least one integrated circuit, the integrated circuit comprising multiple channels for analog to digital conversion of the analog signals and being disposed on the circuit board, each channel converting the analog signal of a single x-ray sensitive cell, wherein the step of converting the analog signals to digital data comprises, for each x-ray sensitive cell:

storing a first value representing a number of pulses during a time period, the pulses occurring when the analog signal from each cell reaches a threshold value; and storing a second value indicative of the time between two pulses that occur during the time period.

66. A method of medical imaging according to claim 65 further comprising the step of assuring that at least two pulses occur during the time period.

67. A method of CT imaging comprising:

rotating an x-ray source about an examination region;

projecting x-rays through the examination region using the x-ray source;

detecting the projected x-rays using a plurality of two-dimensional arrays of x-ray sensitive cells, the arrays of x-ray sensitive cells being disposed on a plurality of circuit boards, each x-ray sensitive cell generating an analog signal indicative of the x-rays detected by said cell; and generating digital signals indicative of the analog signals using a plurality of integrated circuits, the integrated circuits being disposed on the circuit boards and each integrated circuit comprising a plurality of channels, each channel converting to digital the analog signal from not more than one x-ray sensitive cell, wherein each channel of the integrated circuits comprises:

a ratiometric current to frequency converter; and a frequency to digital converter for generating a number of electrical pulses during a time period, the number of pulses being proportional to the magnitude of the analog signal.

68. A method of CT imaging according to claim 67 further comprising generating a first digital value indicative of the number of electrical pulses during the time period and second digital value indicative of a period of time between a first pulse and a second pulse occurring during the time period.

69. A modular radiation detector unit for use in computerized tomographic imaging comprising:

a circuit board;

a plurality of x-ray sensitive cells disposed on the circuit board, the x-ray sensitive cells for receiving x-rays after the x-rays have passed through an examination region and generating an analog signal indicative of the x-rays received thereby; and at least one integrated circuit disposed on the circuit board, the integrated circuit comprising a plurality of analog to digital conversion channels for converting the analog signals from a plurality of x-ray sensitive cells to digital data, wherein each channel comprises:

a current to frequency converter for generating a number of electrical pulses during a time period, the number of pulses being proportional to the magnitude of the analog signal converted by said channel; and a frequency to digital converter which generates a first digital value indicative of the number of pulses generated during the time period and a second digital value indicative of a period of time between pulses of the time period.

70. A modular radiation detector unit according to claim 69 wherein each channel comprises a parallel to serial converter which outputs the first and second digital values in a serial output stream.

71. A modular radiation detector unit according to claim 70 wherein the parallel to serial converters are interconnected to generate a serial output of the digital data of a plurality of channels.

72. A modular radiation detector unit for use in CT imaging comprising:

a circuit board;

a plurality of x-ray sensitive cells disposed on the circuit board for receiving x-rays after the x-rays have passed through an examination region and for generating analog signals indicative of the x-rays received thereby;

a plurality of integrated circuits disposed on the circuit board and in electrical connection with the x-ray sensitive cells, the integrated circuits comprising a plurality of channels, each channel being connected with a single x-ray sensitive cell for receiving the analog signal generated by the x-ray sensitive cell and for converting the analog signal to first digital data;

means for receiving second digital data from a second modular radiation detector unit, the second digital data being indicative of the x-rays received at the second modular radiation detector unit; and means for outputting the first and second digital data to a third modular radiation detector unit, wherein each channel comprises:

a ratiometric current to frequency converter for generating a number of electrical pulses during a time period, the number of pulses being proportional to the magnitude of the analog signal received by the channel; and a frequency to digital converter for generating a first digital value indicative of the number of pulses generated during the time period and a second digital value indicative of a period of time between a first pulse and a last pulse during the time period.

73. A modular radiation detector unit according to claim 72 further comprising means to assure that the value of the first digital value is at least two.

74. A modular radiation detector unit according to claim 73 wherein each channel further comprises parallel to serial converters for outputting the digital data in a serial output stream.

* * * * *